United States Patent
Beech, Jr. et al.

(10) Patent No.: US 7,816,575 B2
(45) Date of Patent: Oct. 19, 2010

(54) REMOVAL OF CATALYST FINES FROM A REACTION SYSTEM

(75) Inventors: James H. Beech, Jr., Kingwood, TX (US); Yun-feng Chang, Houston, TX (US); Michael P. Nicoletti, Houston, TX (US)

(73) Assignee: ExxonMobil Chemical Patents, Inc., Houston, TX (US)

( * ) Notice: Subject to any disclaimer, the term of this patent is extended or adjusted under 35 U.S.C. 154(b) by 953 days.

(21) Appl. No.: 11/651,815

(22) Filed: Jan. 10, 2007

(65) Prior Publication Data

US 2007/0197845 A1   Aug. 23, 2007

Related U.S. Application Data

(60) Provisional application No. 60/774,398, filed on Feb. 17, 2006.

(51) Int. Cl.
*C07C 1/00* (2006.01)
(52) U.S. Cl. .................... 585/639; 585/638; 585/640; 585/910; 502/64; 95/271
(58) Field of Classification Search .............. 585/638, 585/639, 640, 910; 502/64; 95/271
See application file for complete search history.

(56) References Cited

U.S. PATENT DOCUMENTS

| | | | |
|---|---|---|---|
| 5,032,154 A * | 7/1991 | Wright | 422/109 |
| 6,777,585 B2 | 8/2004 | Van Egmond | |
| 6,844,291 B2 | 1/2005 | Levin et al. | |
| 6,884,863 B2 | 4/2005 | Van Egmond | |
| 7,071,136 B2 | 7/2006 | Chang et al. | |
| 7,119,241 B2 | 10/2006 | Beech, Jr. et al. | |
| 2004/0102669 A1 | 5/2004 | Van Egmond | |
| 2004/0235649 A1 | 11/2004 | Chang et al. | |
| 2005/0006539 A1 | 1/2005 | Fischer et al. | |
| 2005/0054516 A1 * | 3/2005 | Vaughn et al. | 502/64 |
| 2007/0157807 A1 * | 7/2007 | Castagnos et al. | 95/271 |

OTHER PUBLICATIONS

"Lower catalyst resistivities raise precipitator efficiencies," Oil & Gas Journal, pp. 78-79, Aug. 10, 1998.

* cited by examiner

*Primary Examiner*—Prem C Singh
(74) *Attorney, Agent, or Firm*—Kevin M. Faulkner

(57) ABSTRACT

This invention provides a process for limiting the loss of catalyst particles through olefin product streams and regenerator flue gas streams exiting the reaction system. In particular, this invention provides for removing catalyst particles from the reactor using a water stream and from the regenerator using a two step separation process. The two step process involves the use of a catalyst fine separation unit.

34 Claims, 4 Drawing Sheets

REMOVAL OF CATALYST FINES FROM A REACTION SYSTEM

CROSS REFERENCE TO RELATED APPLICATIONS

This application claims priority to Provisional application filed on Feb. 17, 2006, U.S. Ser. No. 60/774,398.

FIELD OF THE INVENTION

This invention relates to a process for removing catalyst particles from an oxygenate to olefins reaction system. In particular, this invention relates to a two step process for removing catalyst particles from a regenerator portion of an oxygenate to olefins reaction system.

BACKGROUND OF THE INVENTION

Oxygenate to olefins reaction systems typically convert oxygenates to olefins products. In particular, methanol to olefins reaction systems utilize methanol as the primary feed for the conversion process, and these processes typically use molecular sieves as catalysts.

U.S. Pat. No. 7,071,136 discloses molecular sieves containing [$AlO_4$] and [$SiO_4$] tetrahedral units can be used as a catalyst to convert methanol to olefins such as ethylene and propylene. The particular catalysts are considered to be highly attrition resistant, which is a preferred characteristic for the operation of the reaction system.

U.S. Pat. No. 6,844,291 B2 discloses a molecular sieve catalyst composition that includes a metal oxide. Combining the metal oxide with the molecular sieve was considered to enhance olefin yield and catalyst lifetime in the oxygenate to olefin reaction process.

The oxygenates to olefins process is typically carried out in a fluid bed reactor and regenerator system. The catalyst particles used in the process typically range in particle size from 1 to 200 microns. An average particle size is on the order of 75 microns. Due to catalyst attrition and retention efficiency there is a tendency for catalyst particles, particularly fine catalyst particles on the order of 20 microns or smaller, to be lost from the system exiting with both the reactor and regenerator vapor effluent streams.

"Lower catalyst resistivities raise precipitator efficiencies," *Oil & Gas Journal*, Aug. 10, 1998, pp. 78-79, describe the use of electrostatic precipitators to separate catalyst particles from fluid catalytic cracking units. It is desirable, however, to provide processes to reduce catalyst loss in olefin product and regenerator flue gas streams in oxygenate to olefins reaction systems.

SUMMARY OF THE INVENTION

This invention provides a process for limiting the loss of catalyst particles through olefin product streams and regenerator flue gas streams exiting the reaction system. The invention allows catalyst particles to be removed from the product and flue gas streams so that downstream contamination is minimized.

According to one aspect of the invention, there is provided a process for removing molecular sieve catalyst particles containing [$AlO_4$] and [$SiO_4$] tetrahedral units from an oxygenate to olefin reaction system having a reactor and regenerator. The steps of the process includes separating the molecular sieve catalyst particles from a flue gas stream in the regenerator so that the flue gas stream exits the regenerator at an average catalyst loading of greater than or equal to 10 mg/$NM^3$. The flue gas stream exiting the regenerator is then flowed through a catalyst fine separation unit to form a final flue gas stream having an average catalyst loading of less than that of the stream exiting the regenerator.

In another aspect, there is provided a process for removing molecular sieve catalyst particles that includes a step of contacting the catalyst particles with an oxygenate stream in the reactor to form an olefin product. The olefin product is contacted with a water stream in a quench column to remove catalyst particles entrained in the olefin product, and at least a portion of the catalyst particles is separated from a flue gas stream in the regenerator. The flue gas stream exiting the regenerator is then flowed through a catalyst fine separation unit and a final flue gas stream is recovered at an average catalyst loading less than that of the flue gas stream from the regenerator.

In one embodiment, the catalyst is separated in the regenerator using a cyclone separation system. Preferably, the catalyst fine separation unit is an electrostatic precipitator.

In another embodiment, the electrostatic precipitator is operated at a temperature of at least 250° C. Preferably, the electrostatic precipitator is operated at a catalyst resistivity of not greater than $10^{12}$ ohm-cm. More preferably, the molecular sieve catalyst comprises an electrostatic charging modifier that provides a catalyst resistivity of not greater than $10^{12}$ ohm-cm. Still more preferably, the electrostatic charging modifier includes at least one metal oxide and the catalyst particles have a $TOF_{redox}$ of not greater than 1000 sec$^{-1}$, measured at 100° C. The electrostatic charging modifier is preferably selected from the group consisting of $Cr_2O_3$, $V_2O_5$, $Fe_2O_3$, NiO, ZnO, $SnO_2$, $MoO_3$, $TeO_2$, $Sb_2O_3$, $ZrO_2$, and $CeO_2$.

In yet another embodiment, the molecular sieve catalyst comprises at least one metal oxide electrostatic charging modifier in an amount of at least 50 ppm, based on total weight of the catalyst. In another, a gas stream is added to the electrostatic precipitator to provide a catalyst resistivity of not greater than $10^{12}$ ohm-cm. In another, a water stream is added to the electrostatic precipitator and the electrostatic precipitator is operated at water dew point temperature.

In one embodiment, the catalyst fine separation unit is a filter unit and the filter unit is operated at an average temperature of from 100° C. to 450° C. In another, the catalyst fine separation unit is a wet gas scrubber in which a water stream is injected into the scrubber to remove the catalyst particles and form the final flue gas stream. Preferably, the water stream is taken from a bottoms stream of a methanol stripper.

In another embodiment, the process further comprises contacting the catalyst particles with an oxygenate stream in the reactor to form an olefin product, and contacting the olefin product with a water stream in a quench column to remove catalyst particles entrained in the olefin product. Preferably, a water stream containing catalyst particles is removed from the quench column and sent to a methanol stripper. More preferably, at least a portion of a bottoms water stream from the methanol stripper is sent to the fine separation unit.

BRIEF DESCRIPTION OF THE DRAWINGS

Examples of the invention are provided with reference to the attached Figures, wherein.

DETAILED DESCRIPTION OF THE INVENTION

Catalyst Fines Removal

Figure 1:
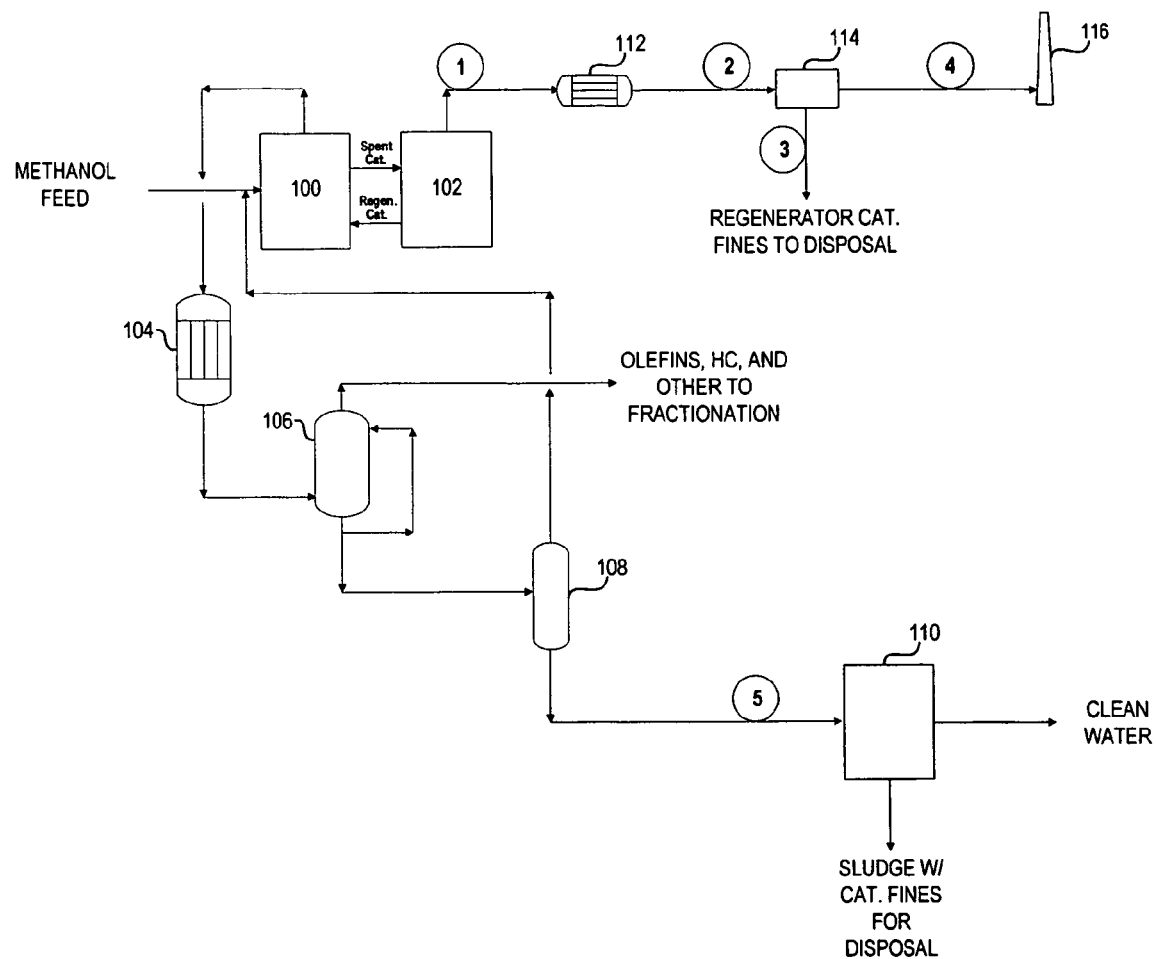
FIG. 1 shows a flow diagram of the invention in which a filter and/or electrostatic precipitator is used as catalyst fine separation unit.

This invention is directed to a process for removing catalyst particles from an oxygenate to olefins reaction system. The reaction system includes one or more reactor units and one or more regenerator units, as well as associated equipment.

In the reactor portion of the system, catalyst particles are contacted with an oxygenate stream to form an olefin product. The reactor portion is preferably operated as a fluid bed reaction system. In such a case, catalyst particles will carry over with the reaction product, and the particles will be separated from the product. In one embodiment, a substantial portion of the catalyst particles is separated from the product in the reactor. However, some portion of the catalyst particles will carry over with the product as the product exits the reactor. A majority of any remaining catalyst particles are removed from the product by contacting the product with a water stream to remove the particles entrained in the olefin product. The water stream that contains the catalyst particles can then be sent to a waste water treatment system.

During the conversion of the oxygenate to olefin, the catalyst particles become covered with a carbonaceous deposit (i.e., coke). This coke deposit is removed from the catalyst by sending the coked catalyst from the reactor portion to a regenerator portion. In the regenerator portion, oxygen containing gas is contacted with the coked catalyst to combust the carbon material, and form a flue gas combustion product. A majority of the catalyst particles is separated from the flue gas within the regenerator portion, and the flue gas is allowed to exit the regenerator.

In one embodiment, the catalyst particles are separated from a flue gas stream in the regenerator so that the flue gas stream that exits the regenerator has an average catalyst loading of greater than or equal to 10 mg/NM$^3$. Additional fine catalyst particles are removed from the flue gas stream exiting the regenerator portion in a second or subsequent step. Preferably, in this second or subsequent step, the flue gas stream exiting the regenerator is flowed through a catalyst fine separation unit to form a final flue gas stream that has an average catalyst loading less than that of the flue gas stream exiting the regenerator.

According to this invention, the unit "mg/NM$^3$" means milligrams per "normal" cubic meters. The term "normal" refers to a temperature of 0° C. and a pressure of 1.013 bar, the conditions at which one mole of an ideal gas has a volume of 22.413837 liters.

Also according to this invention, "fine" catalyst particles refers to particles that have an average diameter of less than 20 microns. A major portion of the particles removed from the flue gas stream exiting the regenerator is considered fine catalyst particles.

In another embodiment, the catalyst particles are separated from a flue gas stream in the regenerator so that the flue gas stream exits the regenerator containing catalyst particles having a $d_{90}$ in a range of from 20 microns to 100 microns. Preferably, the catalyst particles are separated from a flue gas stream in the regenerator so that the flue gas stream exits the regenerator containing catalyst particles having a $d_{90}$ in a range of from 30 microns to 80 microns, more preferably in a range of from 40 microns to 60 microns. As used herein, $d_{90}$ is the average diameter in which the cumulative column of the sample reaches 90% of the total.

In one embodiment, the final flue gas stream exiting the catalyst fine separation unit has a $d_{90}$ in a range of from 0.5 microns to 15 microns. Preferably, the final flue gas stream exiting the catalyst fine separation unit has a $d_{90}$ in a range of from 1 micron to 10 microns, more preferably from 1.5 microns to 5 microns.

Reactor Process and Catalyst Fines Removal

The process of the invention is generally referred to as the gas-to-olefins (GTO) process or, alternatively, the methanol-to-olefins (MTO) process. In this process, an oxygenated feedstock is converted in the presence of a molecular sieve catalyst composition into one or more olefin(s). In particular, the feedstock contains one or more oxygenates, more specifically, one or more organic compound(s) containing at least one oxygen atom. Preferably, the oxygenate in the feedstock includes one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of specific types of oxygenates useful in the invention include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In a preferred embodiment, the feedstock contains at least one oxygenate selected from the group consisting of methanol, ethanol, dimethyl ether, and diethyl ether; more preferably the oxygenate feed contains methanol and/or dimethyl ether, and most preferably the oxygenate feed contains methanol.

The feedstock is converted primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

According to the invention, the amount of olefin(s) produced, based on the total weight of hydrocarbon produced, is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example, greater than 75 weight percent, and preferably greater than 78 weight percent. Typically, the amount of ethylene produced in weight percent based on the total weight of hydrocarbon product produced, is greater than 30 weight percent, such as greater than 35 weight percent, for example, greater than 40 weight percent. In addition, the amount of propylene produced in weight percent based on the total weight of hydrocarbon product produced is greater than 20 weight percent, such as greater than 25 weight percent, for example, greater than 30 weight percent, and preferably greater than 35 weight percent.

In addition to the oxygenate component, such as methanol, the feedstock may contain one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example, water, may be used either in a liquid or a vapor form, or a combination thereof. The diluent may be either added directly to the feedstock entering a reactor or added directly to the reactor, or added with the molecular sieve catalyst composition.

The process can be conducted over a wide range of reactor temperatures. For example, average reactor temperatures are in the range of from about 200° C. to about 1000° C. Preferably, the average reactor temperatures are in the range of from about 250° C. to about 800° C.; more preferably from about 250° C. to about 750° C., or from about 300° C. to about 650° C., or from about 350° C. to about 600° C., and most preferably from about 350° C. to about 550° C.

Similarly, the process can be conducted over a wide range of pressures including autogenous pressure. Typically the partial pressure of the oxygenate exclusive of any diluent therein employed in the process is in the range of from about 0.1 kPaa to about 5 MPaa, such as from about 5 kpaa to about 1 MPaa, and preferably from about 20 kpaa to about 500 kpaa.

The weight hourly space velocity (WHSV), defined as the total weight of feedstock excluding any diluents per hour per weight of molecular sieve in the catalyst composition, typically ranges from about 1 $hr^{-1}$ to about 5000 $hr^{-1}$, such as from about 2 $hr^{-1}$ to about 3000 $hr^{-1}$, for example, from about 5 $hr^{-1}$ to about 1500 $hr^{-1}$, and conveniently from about 10 $hr^{-1}$ to about 1000 $hr^{-1}$. In one embodiment, the WHSV is greater than 20 $hr^{-1}$ and, where feedstock contains methanol and/or dimethyl ether, is in the range of from about 20 $hr^{-1}$ to about 300 $hr^{-1}$.

Where the process is conducted in a fluidized bed, the superficial gas velocity (SGV) of the total feedstock, including diluent and reaction products within the reactor system, and particularly within a riser reactor(s), is at least 0.1 meter per second (m/sec), such as greater than 0.5 m/sec, such as greater than 1 m/sec, for example, greater than 2 m/sec, conveniently greater than 3 m/sec, and typically greater than 4 m/sec.

In an embodiment, the process is carried out as a fluidized bed process (including a turbulent bed process). Preferably, the process is carried out as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in, for example, U.S. Pat. Nos. 4,076,796, 6,287,522 (dual riser), and *Fluidization Engineering*, D. Kunii and O. Levenspiel, Robert E. Krieger Publishing Company, New York, N.Y., 1977.

Preferred reactor types are riser reactors generally described in *Riser Reactor, Fluidization and Fluid-Particle Systems*, pp. 48 to 59, F. A. Zenz and D. F. Othmo, Reinhold Publishing Corporation, New York, 1960, and U.S. Pat. No. 6,166,282 (fast-fluidized bed reactor). In one practical embodiment, the process is conducted as a fluidized bed process or high velocity fluidized bed process.

The overall process is carried out in a reaction system. The reaction system includes a reactor (or reactor portion or reactor unit or units), as well as a regenerator (or regenerator portion or regenerator unit or units). The reactor portion can include one or more riser reactor(s), with the reactor(s) terminating at a disengaging section of the reactor portion. In one embodiment, the one or more riser reactor(s) and disengaging section are contained within a single reactor vessel.

The catalyst particles are contacted with oxygenate in the reactor to form an olefin product and coked catalyst. The coked catalyst is separated from olefin product in the disengaging section, and the separated olefin product stream exits the reactor portion. Typically, catalyst particles, particularly including a majority of fine catalyst particles, are entrained with the olefin product stream exiting the reactor. The product stream exiting the reactor also includes a variety of byproducts, including a substantial amount of water.

In one embodiment, cyclone(s) are provided within the disengaging section of the reactor to separate the coked catalyst composition from the gaseous effluent containing olefin product. Although cyclones are preferred, gravity can also be used to separate the catalyst composition from the gaseous effluent. Other methods for separating the catalyst composition from the gaseous effluent include the use of plates, caps, elbows, and the like.

The coked catalyst is preferably recovered from the disengaging section and can be re-used as is or sent to a regenerator. In the regenerator, the coke or carbonaceous layer is removed by contacting the catalyst, which is still hot from the reaction process, with a regeneration gas to remove some or all of the coke deposit.

The oxygenate to olefin process forms a substantial amount of water as a by-product. Much of this water can be removed by cooling the olefin product stream from the oxygenate reactor to a temperature below the condensation temperature of the water in the stream. Preferably, the temperature of the product stream is cooled to a temperature below the condensation temperature of the oxygenate feed for the oxygenate to olefins process. In certain embodiments, it is desirable to cool the product stream below the condensation temperature of methanol. Preferably, the olefin product stream is cooled to form a water stream and remove catalyst particles entrained in the olefin product.

A quench column is one type of equipment that is effective in cooling the olefin stream from the olefin to oxygenate reaction process. In a quench column, a quenching fluid is directly contacted with the olefin stream to cool the stream to the desired condensation temperature. Condensation produces the condensed water containing stream, which is also referred to as a heavy bottoms stream. The olefin portion of the olefin product stream remains a vapor, and exits the quench column as an overhead vapor stream. The overhead vapor stream is rich in olefin product, and can also contain some oxygenated hydrocarbon by-products as well as water.

In one embodiment, the quenching fluid is a recycle stream of the condensed water containing heavy bottoms stream of the quench column. This water containing stream is desirably cooled, e.g., by a heat exchanger, and injected back into the quench column. It is preferred in this embodiment to not inject cooling medium from an outside source into the quench column, although it may be desirable to do so in other separation equipment down stream of the quench column.

The condensed water stream that exits the quench column will contain a major amount of catalyst particles that enter the quench column along with the olefin product from the reactor. The condensed water stream is then sent to the waste treatment system. Optionally, at least a portion of the condensed water stream is sent to a stripper to remove oxygenate byproducts that can also be found in the water stream. In one embodiment, the stripper is a methanol stripper in which methanol is added to a fractionation column. A vapor stream rich in oxygenate is recovered from the stripper and recycled back to the oxygenate to olefin reactor. A bottoms or liquid stream that exits the stripper contains a major portion of the catalyst particles.

In one embodiment, the liquid stream from either the quench column or stripper is sent to a waste treatment system. Optionally, the waste treatment system separates a solid sludge like material from a clean water stream having a reduced solid content, and the clean water stream is either disposed or at least a portion recycled back to the reaction or recovery system.

In one particular embodiment of the invention, the quenched olefin stream is further processed by compression, preferably multi-staged compression. Two, three, four or more stages can be used, with two or three stages being preferred.

In another embodiment of the invention, the olefin stream is compressed to a pressure that is greater than that at which the oxygenate to olefin reaction process is carried out. Preferably, the olefin stream is compressed to a pressure of at least about 30 psia (207 kPa), more preferably at least about 50 psia (345 kPa), most preferably at least about 100 psia (689 kPa). High pressure ranges are particularly preferred, with the upper limit being a practical one based on cost of design and ease of operation. Practical high pressure limits are generally considered to be up to about 5,000 psia (34,450 kPa), with lower limits of about 1,000 psia (6,895 kPa), about 750 psia (5,171 kPa), and about 500 psia (3,447 kpa) being increasingly preferred. This compressed stream is then sent to additional recovery processes for separating and recovering different olefin product compositions.

Regenerator Process and Catalyst Fines Removal

First Separation Step

Following separation of coked catalyst from gaseous effluent in the reactor system, the coked catalyst is sent to a regenerator. In the regenerator, the coked catalyst is contacted with a regeneration medium, preferably a gas containing oxygen, under conventional regeneration conditions of temperature, pressure and residence time to burn the carbonaceous material from the catalyst particles and form a flue gas composition.

Non-limiting examples of suitable regeneration media include compositions comprising one or more of $O_2$, $O_3$, $SO_3$, $N_2O$, NO, $NO_2$, $N_2O_5$ and $H_2O$. A particularly preferred regeneration medium is one that contains $O_2$, for example, air. Suitable regeneration conditions are those capable of burning coke from the coked catalyst composition, preferably to a level less than 0.5 weight percent, based on the total weight of the catalyst. The regeneration pressure may be in the range of from about 15 psia (103 kpaa) to about 500 psia (3,448 kpaa), such as from about 20 psia (138 kpaa) to about 250 psia (1,724 kpaa), including from about 25 psia (172 kPaa) to about 150 psia (1,034 kpaa), and conveniently from about 30 psia (207 kpaa) to about 60 psia (414 kpaa).

The residence time of the catalyst composition in the regenerator may be in the range of from about one minute to several hours, such as from about one minute to 100 minutes, and the volume of oxygen in the regeneration gas may be in the range of from about 0.01 mole percent to about 5 mole percent based on the total volume of the gas.

The burning of coke in the regeneration step is an exothermic reaction. In one embodiment of the invention, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system.

The regenerated catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, *Experimental Techniques, Circulating Fluidized Beds*, Grace, Avidan and Knowlton, eds., Blackie, 1997 (336-337).

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example, from about 0.2 weight percent to about 5 weight percent, and conveniently from about 0.3 weight percent to about 2 weight percent based on the weight of the molecular sieve in the catalyst.

The catalyst containing the coke, i.e., the coked catalyst, should be contacted with regeneration medium in the regenerator so as to remove at least a portion of the coke, thereby forming a regenerated catalyst. The regenerated catalyst is then re-used to contact oxygenate feed and convert the oxygenate to olefin product. Preferably, the coked catalyst is contacted with regeneration medium in the regenerator at an average regenerator temperature of not greater than about 690° C., more preferably not greater than about 660° C., still more preferably not greater than about 630° C.; and most preferably not greater than about 600° C. The temperature as used herein refers to the average temperature measured in the bed of catalyst contained in the regenerator.

In one embodiment, regenerated catalyst particles are initially separated from the flue gas within the regenerator. Preferably, the coked catalyst is separated from the flue gas in a disengaging section or zone of the regenerator, and the separated flue gas stream exits the regenerator.

In one embodiment, a cyclone separation system is used to separate the regenerated catalyst composition from the flue gas that exits the regenerator. Although cyclones are preferred, gravity effects within the disengaging zone can also be used to separate the catalyst composition from the flue gas effluent. Other methods for separating the catalyst composition from the flue gas effluent include the use of plates, caps, elbows, and the like.

In one embodiment, the disengaging zone is used to separate a major amount of solids from the flue gas, and the flue gas stream that exits the regenerator has an average catalyst loading of greater than or equal to 10 mg/NM$^3$, preferably greater than 20 mg/NM$^3$. In another embodiment, the flue gas stream that exits the regenerator has an average catalyst loading of not greater than 200 mg/NM$^3$, preferably not greater than 150 mg/NM$^3$. In another, the flue gas stream that exits the regenerator has an average catalyst loading of from 10 mg/NM$^3$ to 200 mg/NM$^3$. Preferably, one or more cyclones are used in the disengaging zone of the regenerator to separate the catalyst particles from the flue gas.

Second Separation Step

In one embodiment of the invention, a second separation step to remove additional catalyst particles from flue gas, particularly catalyst fine particles, is used. In the second step, the flue gas exiting the regenerator is flowed through a catalyst fine separation unit. This unit removes a major amount of catalyst fines to form a final flue gas stream having an average catalyst loading less than that following the first separation step. Preferably, the final flue gas stream has an average catalyst loading of less than 50 mg/NM$^3$, more preferably less than 10 mg/NM$^3$.

In one embodiment, the catalyst fine separation unit is an electrostatic precipitator. An electrostatic precipitator (ESP) is a system for collecting solid particles, which operates by virtue of the movement of charges immersed in an electric field.

In one embodiment of the invention, the flue gas exiting the regenerator is flowed through a zone in which an electric field is directed transversely to the flow. The electric field is operated at a high voltage where a corona of free electrons is emitted from the negative electrode. Preferably, the electrodes charge the catalyst particles flowing in the flue gas through the precipitator, and the charged particles migrate under the effect of the electric field toward the positive electrode. The electrode is preferably designed in the form of collecting plates on which the catalyst particles are deposited. The catalyst particles are electrically discharged at the positive electrodes, and the plates, optionally, shaken, so that the collected catalyst particles fall into a hopper located below the plates.

Preferably, the electrostatic precipitator is operated at lower pressures. In one embodiment, the electrostatic precipitator is operated at pressure of not greater than 5 atm. More preferably, the electrostatic precipitator is operated at pressure not greater than 2 atm.

The electrostatic precipitator can be operated over a wide range of temperatures. The temperature range can be affected by the degree of catalyst resistivity or the degree to which the catalyst particles can be ionized. In one embodiment, at relatively high resistivities, for example, greater than 10$^{11}$ ohm-cm or greater than 10$^{12}$ ohm-cm, preferably greater than 10$^{13}$ ohm-cm, it is preferred to operate the electrostatic precipitator at relatively high temperatures. In a particular embodiment, the ESP is operated at a temperature of at least 400° C., preferably at least 450° C.

In one embodiment of the invention, the electrostatic precipitator is operated at a catalyst resistivity that is low enough to improve separation of the particles in the ESP. In one embodiment, the electrostatic precipitator is operated at a catalyst resistivity of not greater than 10$^{12}$ ohm-cm, preferably not greater than 10$^{11}$ ohm-cm, and most preferably in a range of from 10$^9$ ohm-cm to 10$^{12}$ ohm-cm. In another embodiment, when the ESP is operated at relatively high catalyst resistivity, the ESP is preferably operated at lower temperatures, preferably at a temperature of 250° C. or higher, more preferably 300° C. or higher. Most preferably, the ESP in this operation is at a temperature of not greater than 450° C., and more suitably not greater than 400° C.

The charge on the catalyst particles or the ability of the particle surface to be charged can be modified in a number of ways to increase separation ability of the ESP. In one embodiment, the molecular sieve catalyst comprises an electrostatic charging modifier. Preferably, the modifier not only enhances electrostatic charging ability, but also positively affects the conversion of methanol to olefin, particularly light olefin such as ethylene and propylene.

In another embodiment, the charge on the catalyst particles or the ability of the particle surface to ionize is affected by adding a gas stream to the electrostatic precipitator. Examples of useful gas streams include water, preferably as steam, ammonia, or a combination of water and ammonia.

In one embodiment, wet ESP technology is used. In this embodiment, the ESP is operated at water dew point and with water addition. The addition of the water can be in the form of steam or liquid water or a combination of both. Not being bound by any theory, it is believed that the water addition lowers the particulate resistivity. It is also believed that the water addition also wets the catalyst particles on the collector surfaces, reducing entrainment. Water addition is preferably at a level that permits the electrostatic plates to be washed, limiting particle buildup. Preferably, the wet ESP is operated at a temperature of not greater than 100° C.

In one embodiment, the catalyst fine separation unit is a filter unit such as a baghouse. Preferably, the filter unit is operated at an average temperature of from 100° C. to 450° C., with average temperature being defined as the average of the inlet and outlet temperatures. It is particularly preferred that the filter unit be operated at a temperature below the dew point of the vapor in the filter unit to avoid fouling the filter element, more preferably above 100° C. It is also preferred that the filter unit be operated at a pressure of not greater than 5 atm., more preferably not greater than 2 atm. Examples of filter elements that can be used in this invention include, but are not limited to, woven felt, fiberglass, polypropylene, ceramic fiber, Teflon, Nomex or non woven sintered metal or ceramic, and metal or ceramic foams. The melting point of the filter material will define the upper operating temperature of the filter.

In yet another embodiment, the catalyst fine separation unit is a wet gas scrubber that is used to reduce particle load in the flue gas stream. A wet gas scrubber is an apparatus that provides for mass transfer between a liquid and a gas. An exemplary type of scrubber includes a housing that forms a chamber for the mass transfer process. There is typically provided a conduit or pipe type structure for carrying liquid to the scrubber. This conduit is preferably located on an upper portion of the chamber. The pipe means can include one or more liquid discharge outlets which, in a preferred embodiment, can take the form of sprayers. The sprayers spray the liquid into the top of the scrubber so as to contact the catalyst particles. The liquid is preferably water, and the water can come from any of a variety of sources. The wet gas scrubber acts to remove the catalyst particles so that a flue gas stream low in catalyst loading exits through the outlet.

In one embodiment, the water stream exiting from the methanol stripper described above is used in the wet gas scrubber to contact the flue gas entering the wet gas scrubber. This stream, as any water stream, can be added to the flue gas stream prior to entering the scrubber or can be added as a separate line directly to the scrubber.

In another embodiment, the water stream exiting the methanol stripper is first sent to a waste water treatment plant for further separation of catalyst particles and water. Preferably, the water stream from the methanol stripper is sent to a clarification unit where solids are separated from the water. The separated water stream from the waste treatment plant or clarification unit is then contacted with the flue gas at the wet gas scrubber to further remove catalyst particles from the flue gas and form the final flue gas stream.

Catalyst Description

This invention incorporates the use of catalyst containing one or more types of molecular sieve compositions, particularly those types of molecular sieves that contain active catalytic sites that are susceptible to deactivation due to contact with water molecules. In general, molecular sieves have various chemical, physical, and framework characteristics, and have been well classified by the Structure Commission of the International Zeolite Association according to the rules of the IUPAC Commission on Zeolite Nomenclature. A framework-type describes the topology and connectivity of the tetrahedrally coordinated atoms constituting the framework, and makes an abstraction of the specific properties for those materials. Framework-type zeolite and zeolite-type molecular sieves for which a structure has been established, are assigned a three letter code and are described in the *Atlas of Zeolite Framework Types,* 5th edition, Elsevier, London, England (2001).

Crystalline molecular sieve materials all have a 3-dimensional, four-connected framework structure of corner-sharing $TO_4$ tetrahedra, where T is any tetrahedrally coordinated cation. Molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition,* Vol. 137, pp. 1-67, Elsevier Science, B.V., Amsterdam, Netherlands (2001).

Non-limiting examples of molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW, and SOD. Non-limiting examples of preferred molecular sieves, particularly for converting an oxygenate containing feedstock into olefin(s), include AEI, AFI BEA, CHA, EDI, FAU, FER, GIS, LTA, LTL, MER, MFI, MOR, MTT, MWW, and TON. In one preferred embodiment, the molecular sieve of the invention has an AEI topology or a CHA topology, or a combination thereof, most preferably a CHA topology.

The small, medium and large pore molecular sieves have from a 4-ring to a 12-ring or greater framework type. Typically, the molecular sieves employed herein have 8-, 10- or 12-ring structures and an average pore size in the range of from about 3 Å to 15 Å. More typically, the molecular sieves used in this invention have 8 rings and an average pore size less than about 5 Å, such as in the range of from 3 Å to about 5 Å, for example, from 3 Å to about 4.5 Å, and particularly from 3.5 Å to about 4.2 Å.

In one embodiment, molecular sieve crystals that are incorporated into the catalyst have a chabazite (CHA) structure, and the crystals are preferably made of a composition having a molar relationship within the structure of:

$$X_2O_3{:}(n)YO_2,$$

wherein X is a trivalent element, such as aluminum, boron, iron, indium, and/or gallium, preferably aluminum; Y is a tetravalent element, such as silicon, tin, titanium and/or germanium, preferably silicon; and n is greater than 10, preferably greater than 50, still more preferably greater than 100, preferably that ranges from about 10 to about 2,000, more preferably from about 50 to about 600, most preferably from about 100 to about 300.

The molecular sieve that can be incorporated into the catalyst of this invention is prepared from a reaction mixture containing sources of water, an oxide of a trivalent element X, an oxide of a tetravalent element Y, and an organic templating agent or template. In general, templating agents or templates include compounds that contain elements of Group 15 of the Periodic Table of Elements, particularly nitrogen, phosphorus, arsenic, and antimony. Typical templates also contain at least one alkyl or aryl group, such as an alkyl or aryl group having from 1 to 10 carbon atoms, for example, from 1 to 8 carbon atoms. Preferred templates are nitrogen-containing compounds, such as amines, quaternary ammonium compounds, and combinations thereof. Suitable quaternary ammonium compounds are represented by the general formula $R_4N^+$, where each R is hydrogen or a hydrocarbyl or substituted hydrocarbyl group, preferably an alkyl group or an aryl group having from 1 to 10 carbon atoms.

Non-limiting examples of templates include tetraalkyl ammonium compounds including salts thereof, such as tetramethyl ammonium compounds, tetraethyl ammonium compounds, tetrapropyl ammonium compounds, and tetrabutylammonium compounds, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2) octane, N', N',N,N-tetramethyl-(1,6)hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2) octane ion; di-n-butylamine, neopentylamine, di-n-pentylamine, isopropylamine, t-butyl-amine, ethylenediamine, pyrrolidine, and 2-imidazolidone. Preferred templates are selected from the group consisting of tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine, heated degraded forms thereof, and combinations thereof. In one embodiment, the template is preferably selected from the group consisting of N-alkyl-3-quinuclidinol, N,N,N-trialkyl-1-adamantammonium cations, N,N,N-trialkyl-exoaminonorbornane and mixtures thereof, and is preferably a N,N, N-tri-methyl-1-adamantammonium cation.

In general, molecular sieve crystals that are incorporated into the catalyst have a molecular framework that includes $[AlO_4]$ and $[SiO_4]$ tetrahedral units. Such molecular sieves include aluminosilicates, particularly those having a chabazite structure.

In another embodiment, molecular sieve crystals that are incorporated into the catalyst have a molecular framework that includes $[AlO_4]$, $[PO_4]$ and $[SiO_4]$ tetrahedral units, such as silicoaluminophosphates (SAPO), and metal-substituted SAPO molecular sieves. Suitable metal substituents are alkali metals of Group IA of the Periodic Table of Elements, an alkaline earth metals of Group IIA of the Periodic Table of Elements, a rare earth metals of Group IIIB, including the Lanthanides: lanthanum, cerium, praseodymium, neodymium, sanarium, europium, gadolinium, terbium, dysprosium, holmium, erbium, thulium, ytterbium and lutetium; and scandium or yttrium of the Periodic Table of Elements, transition metals of Groups IVB, VB, VIB, VIIB, VIIIB, and IB of the Periodic Table of Elements and mixtures of any of these metal species. In one embodiment, the metal is selected from the group consisting of Co, Cr, Cu, Fe, Ga, Ge, Mg, Mn, Ni, Sn, Ti, Zn and Zr, and mixtures thereof. The metal atoms may be inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the catalyst includes silicoaluminophosphate or metal-containing silicoaluminophosphate molecular sieve crystals. Preferably, the SAPO has a Si/Al ratio less than 0.65, such as less than 0.40, for example, less than 0.32, and particularly less than 0.20. In one embodiment, the molecular sieve has a Si/Al ratio in the range of from about 0.65 to about 0.10, such as from about 0.40 to about 0.10, for example, from about 0.32 to about 0.10, and particularly from about 0.32 to about 0.15.

Non-limiting examples of SAPO molecular sieves useful herein include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56 and metal containing molecular sieves thereof. Of these, particularly useful molecular sieves are SAPO-18, SAPO-34, SAPO-35, SAPO-44, SAPO-56, and metal containing derivatives thereof. SAPO-34 is particularly preferred.

In another embodiment of the invention, the catalyst used in this invention incorporates aluminophosphate (AlPO) molecular sieves. These molecular sieves can be included as separate crystals or they can be intermixed with other crystalline structures such as by an intergrowth structure. Examples of aluminophosphates include AlPO-5, AlPO-11, AlPO-18, AlPO-31, AlPO-34, AlPO-36, AlPO-37, and AlPO-46.

In one embodiment, the catalyst includes a combination of at least one SAPO and at least one AlPO molecular sieve, wherein the SAPO is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47 and SAPO-56, and the AlPO is selected from the group consisting of AlPO-5, AlPO-11, AlPO-18, AlPO-31, AlPO-34, AlPO-36, AlPO-37, and AlPO-46. The sieves can be combined as separate crystals or as intergrown crystals. Preferably, the SAPO is SAPO-18 or SAPO-34, and preferably, the AlPO is AlPO-34 or AlPO-18.

Additional examples of intergrowth molecular sieves useful in this invention include those described in U.S. Patent Application Publication No. 2002-0165089 and International Publication No. WO 98/15496, published Apr. 16, 1998, the descriptions of those sieves incorporated herein by reference. Note that SAPO-18, AlPO-18 and RUW-18 have an AEI framework-type, and SAPO-34 has a CHA framework-type.

Preferred molecular sieves used in this invention can comprise at least one intergrowth phase of AEI and CHA framework-types. Particularly preferred intergrowths are those in which the ratio of CHA framework-type to AEI framework-type, as determined by the DIFFaX method disclosed in U.S. Patent Application Publication No. 2002-0165089, is greater than 1:1.

As noted above, in one embodiment, the molecular sieve catalyst comprises an electrostatic charging modifier. Preferably, the modifier not only enhances electrostatic charging ability, but also positively affects the conversion of methanol to olefin, particularly light olefin such as ethylene and propylene.

In one embodiment, the electrostatic charging modifier is a metal oxide that provides a reduction in catalyst resistivity. Preferably, the metal oxide modified catalyst has relatively low methanol oxidation (TOF$_{redox}$) and is relatively low in methoxy decomposition.

In one embodiment, the catalyst particles include a metal oxide and the catalyst particles have a TOF$_{redox}$ of not greater than 1000 sec$^{-1}$, measured at 100° C., preferably not greater than 500 sec$^{-1}$, more preferably not greater than 100 sec$^{-}$, still more preferably not greater than 10 sec$^{-1}$, and most preferably not greater than 1 sec$^{-1}$. In another embodiment, the catalyst particles include a metal oxide and the catalyst particles have a methoxy decomposition temperature of at least 100° C., preferably at least 200° C., more preferably at least 300° C. The activity for decomposition of the methoxy group and conversion of methanol to oxygenates including dimethyl ether (DME) and carbon dioxide are preferably determined by the method of Badlani, Birand, and Wachs, "Methanol: A 'Smart' Chemical Probe Molecule," presented in the 2001 Spring Symposium of the Catalysis Society of New York Metropolitan, Lehigh University, Lehigh, Pa., March, 2000. Reactivity of methanol conversion is preferably measured by chemisorption of methanol at 100° C. carried out in a thermal gravimetric analyzer (TGA) and subsequent temperature programmed reaction (TPR). The products formed from the TPR are measured using an on-line GC. Formation rate for HCHO, HCOOCH$_3$, and CH$_2$(OCH$_3$)$_2$ is defined as redox acitivity TOF$_{redox}$ (turnover frequency).

In one embodiment of the invention, the molecular sieve catalyst includes at least one metal oxide electrostatic charging modifier selected from the group consisting of Cr$_2$O$_3$, V$_2$O$_5$, Fe$_2$O$_3$, NiO, ZnO, SnO$_2$, MoO$_3$, TeO$_2$, Sb$_2$O$_3$, ZrO$_2$, and CeO$_2$ Preferably, the molecular sieve catalyst includes at least one metal oxide electrostatic charging modifier selected from the group consisting of TeO$_2$, Sb$_2$O$_3$, ZrO$_2$, and CeO$_2$, more preferably ZrO$_2$, and CeO$_2$ Particularly preferred molecular sieve catalysts are those that include [AlO$_4$] and [SiO$_4$] tetrahedral units, and, optionally, [PO$_4$] tetrahedral units, as well as contain one or more of the metal oxide electrostatic charging modifiers or their structural derivatives.

In a particular embodiment, the molecular sieve catalyst includes at least one metal oxide electrostatic charging modifier in an amount of at least 50 ppm, based on total weight of the catalyst. Preferably, the molecular sieve catalyst includes at least one metal oxide electrostatic charging modifier in an amount of at least 100 ppm, more preferably at least 200 ppm, based on total weight of the catalyst.

In an embodiment, the metal oxides are derived from transformation of their corresponding salts. Examples of the corresponding salts include nitrate, nitrite, sulfate, chloride, phosphate, carbonate, oxalate, hydroxide, acetate, or other organometallic forms. Transformation of the salt forms to the metal oxide material involves thermal or hydrothermal treatment at a temperature greater than 100° C., more preferably at a temperature greater than 200° C., and most preferably at a temperature greater than 350° C.

The critical temperature of the catalyst is preferably measured below 400° C., and more preferably below 300° C., and most preferably below 250° C. The critical temperature of the catalyst is the temperature at which catalyst conductivity changes from a mechanism dominated by surface conduction to volumetric conduction.

In one embodiment, electrostatic charging reduction modifier is added to the catalyst in an amount not greater than 10 wt % as metal oxide. Preferably, electrostatic charging reduction modifier is added to the catalyst in an amount not greater than 8 wt %, and more preferably not greater than 6 wt %.

EXAMPLES

Example 1

An example of a high temperature electrostatic precipitator (ESP) was run according to the flow diagram shown in FIG. 1, and using standard material balance procedures.

As shown in FIG. 1, methanol feed is sent to a reactor 100. Spent or coked catalyst is separated from olefin product in the reactor 100, preferably in a disengaging zone in the reactor 100. Olefin product, which includes a significant amount of water, byproduct and some catalyst fines, is sent to a cooler 104, and the cooled product is sent to a quench tower 106. At the quench tower 106, water is condensed from the olefin and other hydrocarbon vapors. The olefin and hydrocarbon vapors are then sent on to recovery, preferably by fractionation.

A portion of the condensed water stream from quench tower 106 is also recycled and preferably further cooled in the recycle. The condensing of the water and the additional contact of the recycled water stream aid to remove catalyst fines that had, been entrained in the olefin product. The condensed water stream includes not only catalyst fines, but condensable hydrocarbons such as unconverted methanol. This stream is sent to methanol stripper 108, which separates methanol and lighter hydrocarbons from the water and solids. The methanol and lighter hydrocarbons are recycled back to the reactor 100 as feed, and the water and solids stream 5 is sent to a waste treatment system 110. The waste treatment system preferably includes a solids settler that aids in separating the solid catalyst particles from the water. The separated or clean water is then discharged or at least a portion can be recycled or reused in the system. See FIGS. 2 and 3, which are further detailed in the following examples.

Coke material is removed from the catalyst in the regenerator 102 by burning in the presence of an oxygen containing gas to form a flue gas. The flue gas is separated from the regenerated catalyst in a first separation step within the regenerator, preferably using a cyclone system. Flue gas containing catalyst fine particles exit the regenerator 102 through a line 1. The flue gas is cooled by a heat exchanger 112. This can be a low pressure exchanger that produces low pressure steam or more that one exchanger can be used to produce low and high pressure steam.

The cooled flue gas containing the catalyst fine particles is then sent to a catalyst fine separation unit 114, in this example a high temperature ESP. The high temperature ESP is operated at high temperature to remove a major amount of the catalyst fines from the flue gas, stream 3. A final flue gas composition, stream 4, which is low in particulates, is then sent to a flue gas stack 116 and discharged to the atmosphere.

The results of the high temperature ESP run are shown in Table 1.

TABLE 1

| | | Stream No. | | | | |
|---|---|---|---|---|---|---|
| | | 1 | 2 | 3 | 4 | 5 |
| Stream Description | | REGEN FLUE GAS | ESP INLET | COLLECTED FINES | STACK GAS | WASTE WATER STRIPPER BTMS |
| Stream Phase | | VAPOR | VAPOR | SOLID | VAPOR | LIQUID |
| Temperature | F. | 1200 | 850 | 800 | 350 | 302 |
| Pressure | PSIG | 18.0 | 1.0 | 0.4 | 0.0 | 54.6 |
| Total Flow Rates | LB/HR | | | | | |
| Vapor or Liquid | | 515209.8 | 515209.8 | 0.0 | 515209.8 | 1348736.0 |
| Coke | | 0.0 | 0.0 | 0.0 | 0.0 | 6.8 |
| Catalyst | | 8.6 | 8.6 | 8.1 | 0.5 | 164.2 |
| Total Mass Rate | LB/HR | 515218.5 | 515218.5 | 8.2 | 515210.4 | 1348907.0 |
| Vapor Rate | ACFH | 9686132.0 | 15920595.3 | — | 10513694.3 | — |
| | NM³/hr | 180834.1 | 180834.1 | — | 180834.1 | — |
| Cat. Loading in Vapor | mg/NM³ | 21.7 | 21.7 | — | 1.3 | — |
| Cat. Loading in Liquid | PPMW | — | — | — | — | 127 |
| Catalyst Particle Size Distribution Cumulative wt % less than | Microns | | | | | |
| 0.01 | | 0.09 | 0.09 | 0.07 | 0.10 | 0.03 |
| 0.1 | | 0.16 | 0.16 | 0.16 | 0.19 | 0.08 |
| 0.5 | | 0.25 | 0.25 | 0.29 | 0.29 | 0.16 |
| 1 | | 0.32 | 0.32 | 0.38 | 0.35 | 0.2 |

TABLE 1-continued

|  | Stream No. | | | | |
| --- | --- | --- | --- | --- | --- |
|  | 1 | 2 | 3 | 4 | 5 |
| 2 | 0.41 | 0.41 | 0.50 | 0.41 | 0.4 |
| 3 | 0.49 | 0.40 | 0.58 | 0.46 | 0.4 |
| 4 | 0.55 | 0.55 | 0.65 | 0.50 | 0.5 |
| 5 | 0.61 | 0.61 | 0.71 | 0.53 | 0.6 |
| 10 | 0.85 | 0.85 | 0.92 | 0.64 | 1.1 |
| 20 | 1.3 | 1.3 | 1.2 | 1.1 | 2.0 |
| 30 | 1.7 | 1.7 | 1.4 | 1.4 | 4.0 |
| 40 | 2.2 | 2.2 | 1.6 | 1.6 | 10.1 |
| 50 | 2.8 | 2.8 | 2.5 | 1.9 | 16.0 |
| 60 | 4.0 | 4.0 | 6.0 | 2.3 | 22.5 |
| 70 | 9.0 | 9.0 | 12.7 | 2.7 | 30.1 |
| 80 | 31.8 | 31.8 | 24.2 | 3.3 | 37.9 |
| 90 | 48.7 | 48.7 | 42.8 | 3.9 | 46.8 |
| 95 | 56.3 | 56.3 | 55.6 | 4.2 | 54.5 |
| 99 | 67.8 | 67.8 | 67.9 | 4.6 | 71.1 |

Example 2

An example of an electrostatic precipitator (ESP) was run according to the flow diagram as shown in FIG. 1, and using the calculating method of Example 1, except that steam and ammonia were added to stream 2 to reduce catalyst resistivity, and a lower temperature was used. The results are shown in Table 2.

TABLE 2

|  |  | Stream No. | | | | |
| --- | --- | --- | --- | --- | --- | --- |
|  |  | 1 | 2 | 3 | 4 | 5 |
| Stream Description |  | REGEN FLUE GAS | ESP INLET | COLLECTED FINES | STACK GAS | WASTE WATER STRIPPER BTMS |
| Stream Phase |  | VAPOR | VAPOR | SOLID | VAPOR | LIQUID |
| Temperature | F. | 1200 | 582 | 530 | 500 | 302 |
| Pressure | PSIG | 18.0 | 1.0 | 0.4 | 0.0 | 54.6 |
| Total Flow Rates* | LB/HR |  |  |  |  |  |
| Vapor or Liquid |  | 515209.8 | 515209.8 | 0.0 | 515209.8 | 1348736.0 |
| Coke |  | 0.0 | 0.0 | 0.0 | 0.0 | 6.8 |
| Catalyst |  | 8.6 | 8.6 | 8.1 | 0.5 | 164.2 |
| Total Mass Rate* | LB/HR | 515218.5 | 515218.5 | 8.2 | 515210.4 | 1348907.0 |
| Vapor Rate* | AC FH | 9686132.0 | 12663557.5 | — | 12460674.7 | — |
|  | NM$^3$/hr | 180834.1 | 180834.1 | — | 180834.1 | — |
| Cat. Loading in Vapor | mg/NM$^3$ | 21.7 | 21.7 | — | 1.3 | — |
| Cat. Loading in Liquid | PPMW | — | — | — | — | 127 |
| Catalyst Particle Size Distribution Cumulative wt % less than | Microns |  |  |  |  |  |
| 0.01 |  | 0.09 | 0.09 | 0.07 | 0.10 | 0.03 |
| 0.1 |  | 0.16 | 0.16 | 0.16 | 0.19 | 0.08 |
| 0.5 |  | 0.25 | 0.25 | 0.29 | 0.29 | 0.16 |
| 1 |  | 0.32 | 0.32 | 0.38 | 0.35 | 0.2 |
| 2 |  | 0.41 | 0.41 | 0.50 | 0.41 | 0.4 |
| 3 |  | 0.49 | 0.49 | 0.58 | 0.46 | 0.4 |
| 4 |  | 0.55 | 0.55 | 0.65 | 0.50 | 0.5 |
| 5 |  | 0.61 | 0.61 | 0.71 | 0.53 | 0.6 |
| 10 |  | 0.85 | 0.85 | 0.92 | 0.64 | 1.1 |
| 20 |  | 1.3 | 1.3 | 1.2 | 1.1 | 2.0 |
| 30 |  | 1.7 | 1.7 | 1.4 | 1.4 | 4.0 |
| 40 |  | 2.2 | 2.2 | 1.6 | 1.6 | 10.1 |
| 50 |  | 2.8 | 2.8 | 2.5 | 1.9 | 16.0 |
| 60 |  | 4.0 | 4.0 | 6.0 | 2.3 | 22.5 |
| 70 |  | 9.0 | 9.0 | 12.7 | 2.7 | 30.1 |
| 80 |  | 31.8 | 31.8 | 24.2 | 3.3 | 37.9 |

TABLE 2-continued

| | Stream No. | | | | |
|---|---|---|---|---|---|
| | 1 | 2 | 3 | 4 | 5 |
| 90 | 48.7 | 48.7 | 42.8 | 3.9 | 46.8 |
| 95 | 56.3 | 56.3 | 55.6 | 4.2 | 54.5 |
| 99 | 67.8 | 67.8 | 67.9 | 4.6 | 71.1 |

Example 3

Figure 2:
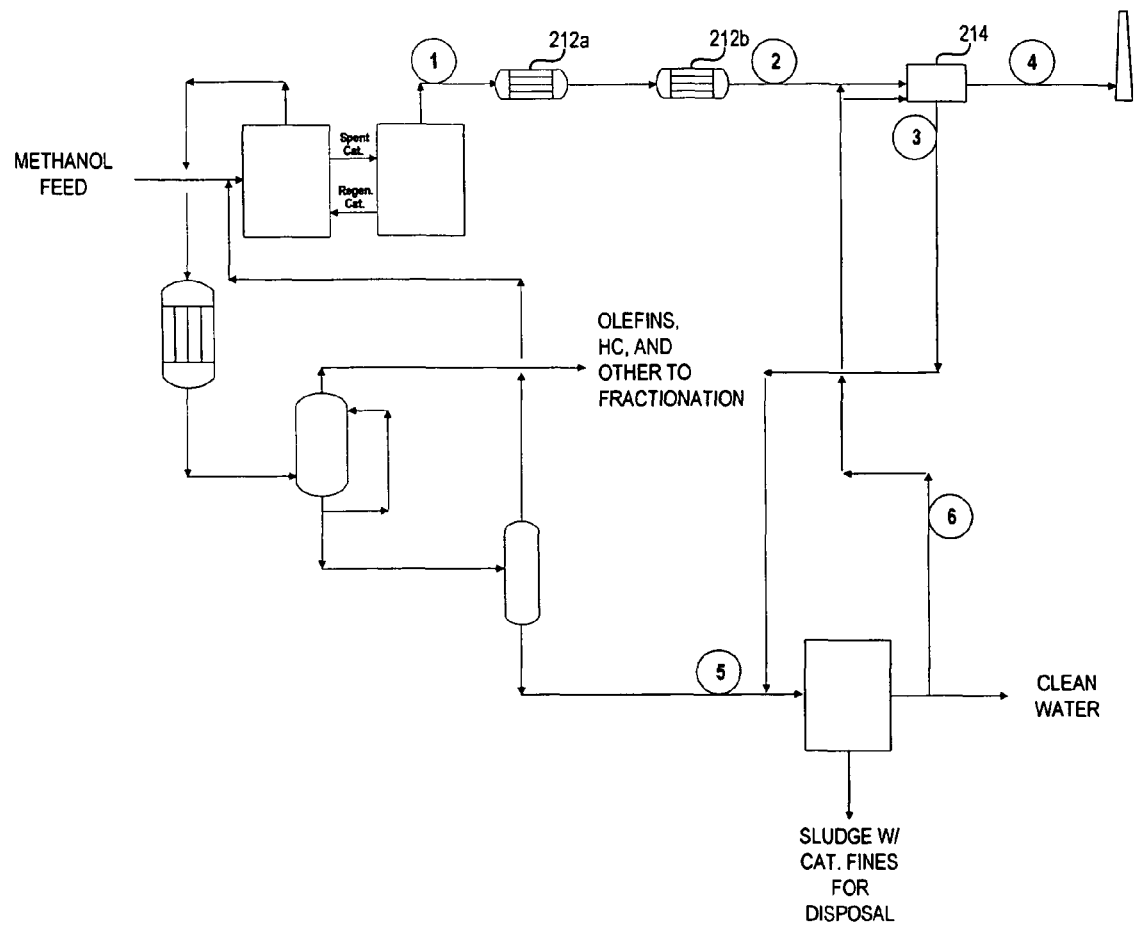
FIG. 2 shows a flow diagram of the invention in which a wet electrostatic precipitator is used as catalyst fine separation unit.

An example of wet ESP (WESP) was run according to the flow diagram as shown in FIG. 2, and using the calculating method of Example 1. The flow diagram in FIG. 2 is like that of FIG. 1, except that catalyst fine separation unit 214 in this example is a WESP, and two heat exchangers are used, high pressure heat exchanger 212a and low pressure heat exchanger 212b. A portion of the clean water stream 6 is sent to the WESP, and a condensed water stream containing catalyst fines is sent as stream 3 back to the waste treatment system.

The WESP is operated at the dew point temperature of the gas stream with water added as both steam and in the liquid form. The added water is believed to lower the particulate resistivity and to also wet the particulates on the collector surfaces reducing entrainment. Unlike dry ESPs, resistivity of the collected material is generally not a major factor in performance. Because of the high humidity in a wet ESP, the resistivity of particles is lowered, eliminating the "back corona" condition. Frequent washing of the plates also limits particle buildup on the collectors. In the embodiment shown in FIG. 2, the flue gas is cooled down to temperatures below 212° F. as the WESP operates at near atmospheric pressure. The results are shown in Table 3.

TABLE 3

| | | Stream No. | | | | | |
|---|---|---|---|---|---|---|---|
| | | 1 | 2 | 3 | 4 | 5 | 6 |
| Stream Description | | REGEN FLUE GAS | FLUE GAS TO WESP | FINES & LIQUID WATER | STACK GAS | WASTE WATER STRIPPER BTMS | WATER TO WESP |
| Stream Phase | | VAPOR | VAPOR | SLURRY | VAPOR | LIQUID | LIQUID |
| Temperature | F. | 1200 | 350 | 140 | 140 | 302 | 100 |
| Pressure | PSIG | 18.0 | 1.0 | 0.4 | 0.0 | 54.6 | 60.0 |
| Total Flow Rates | LB/HR | | | | | | |
| Vapor or Liquid | | 515209.8 | 515209.8 | 84.0 | 542125.8 | 1348736.0 | 27000 |
| Coke | | 0.0 | 0.0 | 0.0 | 0.0 | 6.8 | 0 |
| Catalyst | | 8.6 | 8.6 | 8.4 | 0.3 | 164.2 | 0 |
| Total Mass Rate | LB/HR | 515218.5 | 515218.5 | 92.4 | 542126.1 | 1348907.0 | 27000.0 |
| Vapor Rate | ACFH | 9686132.0 | 9644032.2 | — | 7787921.7 | — | — |
| | NM³/hr | 180834.1 | 180834.1 | — | 180834.1 | — | — |
| Cat. Loading in Vapor | mg/NM³ | 21.7 | 21.7 | — | 0.7 | — | — |
| Cat. Loading in Liquid | PPMW | — | — | — | — | 127 | — |
| Catalyst Particle Size Distribution Cumulative wt % less than | Microns | | | | | | |
| 0.01 | | 0.09 | 0.09 | 0.07 | 0.10 | 0.03 | — |
| 0.1 | | 0.16 | 0.16 | 0.16 | 0.19 | 0.08 | — |
| 0.5 | | 0.25 | 0.25 | 0.29 | 0.28 | 0.16 | — |
| 1 | | 0.32 | 0.32 | 0.38 | 0.34 | 0.2 | — |
| 2 | | 0.41 | 0.41 | 0.49 | 0.41 | 0.4 | — |
| 3 | | 0.49 | 0.49 | 0.58 | 0.46 | 0.4 | — |
| 4 | | 0.55 | 0.55 | 0.65 | 0.49 | 0.5 | — |
| 5 | | 0.61 | 0.61 | 0.70 | 0.52 | 0.6 | — |
| 10 | | 0.85 | 0.85 | 0.91 | 0.63 | 1.1 | — |
| 20 | | 1.3 | 1.3 | 1.2 | 1.1 | 2.0 | — |
| 30 | | 1.7 | 1.7 | 1.4 | 1.3 | 4.0 | — |
| 40 | | 2.2 | 2.2 | 1.6 | 1.6 | 10.1 | — |
| 50 | | 2.8 | 2.8 | 2.2 | 1.9 | 16.0 | — |
| 60 | | 4.0 | 4.0 | 5.6 | 2.2 | 22.5 | — |

TABLE 3-continued

| | Stream No. | | | | | |
|---|---|---|---|---|---|---|
| | 1 | 2 | 3 | 4 | 5 | 6 |
| 70 | 9.0 | 9.0 | 12.0 | 2.7 | 30.1 | — |
| 80 | 31.8 | 31.8 | 23.3 | 3.2 | 37.9 | — |
| 90 | 48.7 | 48.7 | 42.0 | 3.8 | 46.8 | — |
| 95 | 56.3 | 56.3 | 55.0 | 4.1 | 54.5 | — |
| 99 | 67.8 | 67.8 | 67.6 | 4.4 | 71.1 | — |

Example 4

An example of a filter or baghouse is employed similar to the flow scheme shown in FIG. 1, except that the ESP is replaced by a baghouse. Unlike an ESP, baghouse efficiency is unaffected by the resistivity of the catalyst. Baghouse bag material (felt, polymer fabrics) typically imposes a maximum temperature limit of ~450° F. (232° C.), although somewhat higher temperature may be used with more expensive material such as Nomex and fiberglass or even higher temperatures with ceramics or sintered metal filters. Examples of bag materials include felt, woven fiberglass, Nomex, and fiberglass w/PTFE. The unit operates at near atmospheric pressure. The baghouse is operated above the vapor stream dew point [212° F. (100° C.) in this case] to avoid fouling of the bag material. The results are shown in Table 4.

TABLE 4

| | | Stream No. | | | | |
|---|---|---|---|---|---|---|
| | | 1 | 2 | 3 | 4 | 5 |
| Stream Description | | REGEN FLUE GAS | BAGHOUSE INLET | COLLECTED FINES | STACK GAS | WASTE WATER STRIPPER BTMS |
| Stream Phase | | VAPOR | VAPOR | SOLID | VAPOR | LIQUID |
| Temperature | F. | 1200 | 350 | 350 | 350 | 302 |
| Pressure | PSIG | 18.0 | 1.0 | 0.8 | 0.0 | 54.6 |
| Total Flow Rates* | LB/HR | | | | | |
| Vapor or Liquid | | 515209.8 | 515209.8 | 0.0 | 515209.8 | 1348736.0 |
| Coke | | 0.0 | 0.0 | 0.0 | 0.0 | 6.8 |
| Catalyst | | 8.6 | 8.6 | 8.6 | 0.1 | 164.2 |
| Total Mass Rate* | LB/HR | 515218.5 | 515218.5 | 8.6 | 515209.9 | 1348907.0 |
| Vapor Rate* | ACFH | 9686132.0 | 9844032.2 | — | 10513694.3 | — |
| | NM³/hr | 180834.1 | 180834.1 | — | 180834.1 | — |
| Cat. Loading in Vapor | mg/NM³ | 21.7 | 21.7 | — | 0.2 | — |
| Cat. Loading in Liquid | PPMW | — | — | — | — | 127 |

*Resistivity additive components not shown

| Catalyst Particle Size Distribution Cumulative wt % less than | Microns | | | | |
|---|---|---|---|---|---|
| 0.01 | 0.09 | 0.09 | 0.6 | 0.9 | 0.03 |
| 0.1 | 0.16 | 0.16 | 0.16 | 0.17 | 0.08 |
| 0.5 | 0.25 | 0.25 | 0.29 | 0.26 | 0.16 |
| 1 | 0.32 | 0.32 | 0.38 | 0.31 | 0.2 |
| 2 | 0.41 | 0.41 | 0.49 | 0.37 | 0.4 |
| 3 | 0.49 | 0.49 | 0.57 | 0.41 | 0.4 |
| 4 | 0.55 | 0.55 | 0.64 | 0.44 | 0.5 |
| 5 | 0.61 | 0.61 | 0.70 | 0.47 | 0.6 |
| 10 | 0.85 | 0.85 | 0.91 | 0.57 | 1.1 |
| 20 | 1.3 | 1.3 | 1.2 | 0.9 | 2.0 |
| 30 | 1.7 | 1.7 | 1.4 | 1.1 | 4.0 |
| 40 | 2.2 | 2.2 | 1.5 | 1.3 | 10.1 |
| 50 | 2.8 | 2.8 | 2.0 | 1.6 | 16.0 |
| 60 | 4.0 | 4.0 | 5.2 | 1.9 | 22.5 |
| 70 | 9.0 | 9.0 | 11.4 | 2.3 | 30.1 |
| 80 | 31.8 | 31.8 | 22.6 | 2.7 | 37.9 |
| 90 | 48.7 | 48.7 | 41.4 | 3.2 | 46.8 |

TABLE 4-continued

| | Stream No. | | | | |
|---|---|---|---|---|---|
| | 1 | 2 | 3 | 4 | 5 |
| 95 | 56.3 | 56.3 | 54.6 | 3.5 | 54.5 |
| 99 | 67.8 | 67.8 | 67.4 | 3.7 | 71.1 |

Example 5

Figure 3:
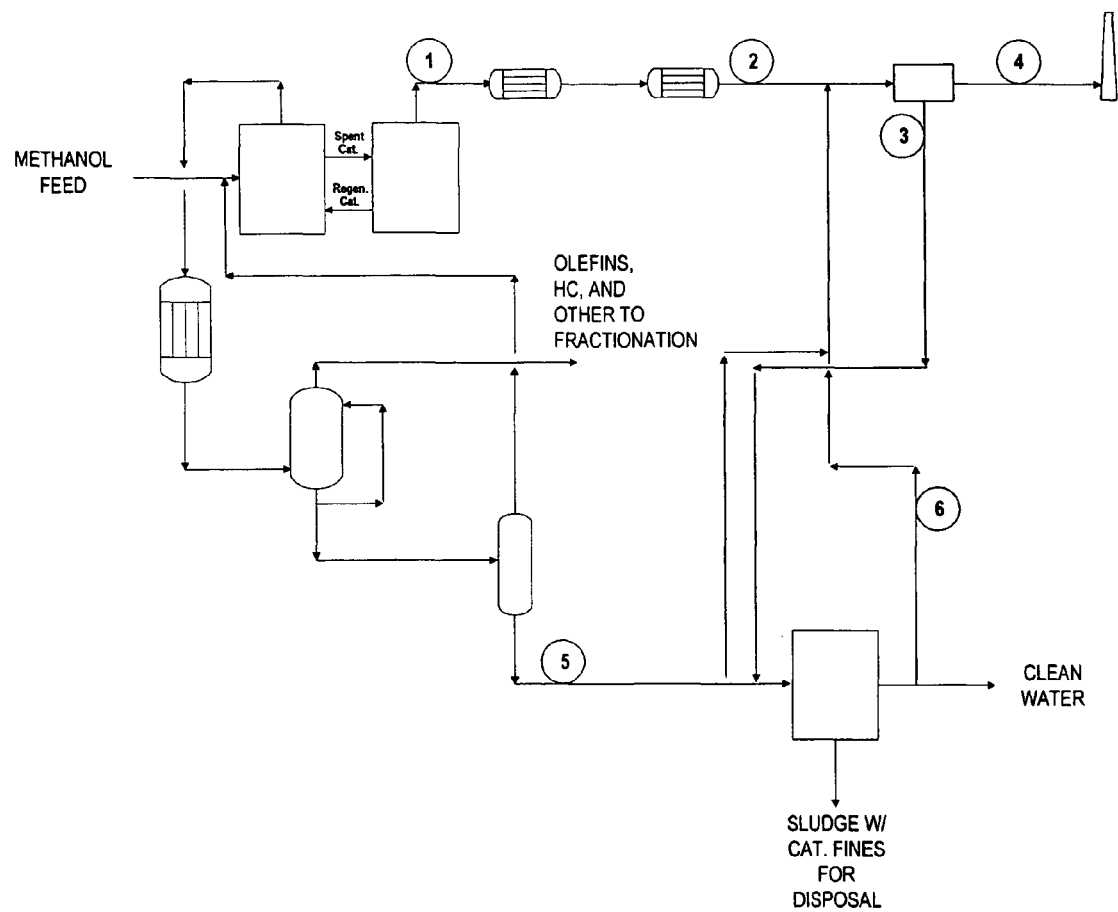
FIG. 3 shows a flow diagram of the invention in which a wet gas scrubber is used as catalyst fine separation unit.

An example of a wet gas scrubber was run according to the flow diagram as shown in FIG. 3, and using the calculating method of Example 1. The flow diagram in FIG. 3 is like that of FIG. 2, except that catalyst fine separation unit 214 in this example is a wet gas scrubber. In addition, a portion of the water stream from the methanol stripper can be used to supply water to the wet gas scrubber.

The wet gas scrubber in this example is run at high capture efficiency, over 90%. Since the captured catalyst fines are in a water liquid slurry, they can be readily added to the waste water stream also containing reactor catalyst fines and disposed of in the waste water treatment plant sludge. The make-up water stream for the wet gas scrubber is shown as being taken from the methanol tower water bottoms stream. This stream is low in organics and also contains catalyst fines in a dilute slurry (135 ppmw). The wet gas scrubber liquid recycle stream can be eliminated and replaced with an equivalent amount of methanol tower water bottoms saving a pump and utilities and the scrubber run with one pass water. Any number of different types of wet gas scrubbers can be used. In this example, a high energy venturi type is preferred due to its high efficiency, and because of the high pressure drop available. Other types of wet gas scrubbers include, spray chamber, centrifugal, baffled towers, packed bed, orifice, and impingement plate types. The results of this run are shown in Table 5.

TABLE 5

| | | Stream No. | | | | |
|---|---|---|---|---|---|---|
| | | 1 | 2 | 3 | 4 | 5 |
| Stream Description | | REGEN FLUE GAS | WET GAS SCRUBBER INLET | FINES & LIQUID RETURN | STACK GAS | WASTE WATER STRIPPER BTMS |
| Stream Phase | | VAPOR | VAPOR | SLURRY | VAPOR | LIQUID |
| Temperature | F. | 1200 | 350 | 350 | 138 | 302 |
| Pressure | PSIG | 18.0 | 2.0 | 0.0 | 0.0 | 54.6 |
| Total Flow Rates | LB/HR | | | | | |
| Vapor or Liquid | | 515209.8 | 515209.8 | 685359.0 | 541820.5 | 1348736.0 |
| Coke | | 0.0 | 0.0 | 3.5 | 0.0 | 6.8 |
| Catalyst | | 8.6 | 8.6 | 92.0 | 0.1 | 164.2 |
| Total Mass Rate | LB/HR | 515218.5 | 515218.5 | 685454.5 | 541820.7 | 1348907.0 |
| Vapor Rate | ACFH | 9686132.0 | 9254569.2 | — | 7761961.9 | — |
| | $NM^3/hr$ | 180834.1 | 180834.1 | — | 180834.1 | — |
| Cat. Loading in Vapor | $mg/NM^3$ | 21.7 | 21.7 | — | 0.3 | — |
| Cat. Loading in Liquid | PPMW | — | — | — | — | 127 |
| Catalyst Particle Size Distribution Cumulative wt % less than | Microns | | | | | |
| 0.01 | | 0.09 | 0.09 | 0.06 | 0.06 | 0.03 |
| 0.1 | | 0.16 | 0.16 | 0.16 | 0.11 | 0.08 |
| 0.5 | | 0.25 | 0.25 | 0.29 | 0.17 | 0.16 |
| 1 | | 0.32 | 0.32 | 0.38 | 0.21 | 0.2 |
| 2 | | 0.41 | 0.41 | 0.49 | 0.26 | 0.4 |
| 3 | | 0.49 | 0.49 | 0.57 | 0.29 | 0.4 |
| 4 | | 0.55 | 0.55 | 0.64 | 0.32 | 0.5 |
| 5 | | 0.61 | 0.61 | 0.70 | 0.34 | 0.6 |
| 10 | | 0.85 | 0.85 | 0.91 | 0.41 | 1.1 |
| 20 | | 1.3 | 1.3 | 1.2 | 0.5 | 2.0 |
| 30 | | 1.7 | 1.7 | 1.4 | 0.6 | 4.0 |
| 40 | | 2.2 | 2.2 | 1.5 | 0.6 | 10.1 |
| 50 | | 2.8 | 2.8 | 2.0 | 0.8 | 16.0 |

TABLE 5-continued

|    | Stream No. | | | | |
|----|------|------|------|-----|------|
|    | 1    | 2    | 3    | 4   | 5    |
| 60 | 4.0  | 4.0  | 5.1  | 1.0 | 22.5 |
| 70 | 9.0  | 9.0  | 11.3 | 1.2 | 30.1 |
| 80 | 31.8 | 31.8 | 22.3 | 1.5 | 37.9 |
| 90 | 48.7 | 48.7 | 40.9 | 1.8 | 46.8 |
| 95 | 56.3 | 56.3 | 53.9 | 2.0 | 54.5 |
| 99 | 67.8 | 67.8 | 66.6 | 2.1 | 71.1 |

Example 6

Examples of catalyst including an electrostatic charging modifier were prepared as follows:

Example 6.1

A slurry containing 45 wt % solid was prepared according to this procedure: (A) adding 991.56 g of SAPO-34 sieve 64Y to 573.15 g of deionized water and mixed at 700 rpm for 10 minutes using a Yamato Model 2100 homogenizer (Yamato Scientific America Inc., Orangeburg, N.Y.), then mixed using a Silverson high-shear mixer at 6000 rpm (Silverson Machines, Inc., East Longmeadow, Mass.) to give a slurry having pH of 6.9; (B) adding 285.39 g of Reach AZP-908 Superultrafine activated zirconium aluminum tetrachlorohydrex GL (Reheis Inc., Berkeley Heights, N.J.) to 286.59 g of deionized water, mixed using Yamato mixer at 700 rpm for 10 minutes. This led to a solution having a pH of 3.1; (C) add content in step (A) to that of step (B) while mixing at 700 rpm for 10 minutes using the Yamato mixer, then mixed using the high-shear Silverson mixer at 6000 rpm for 4 minutes. This resulted in a slurry having pH of 3.6; (D) adding 767.7 g of ASP Ultrafine kaolin clay (Engelhard Corporation, Iselin, N.J.) while under mixing at 700 rpm; continued to mix for 10 minutes resulting in a slurry having pH of 3.6; (E) subjecting the slurry from step (D) to high-shear mixing at 6000 rpm for 4 minutes; (F) adding 95.52 g of deionized water to slurry from step (E), then mixed at 700 rpm for 10 minutes followed with another high-shear mixing at 6000 rpm for 4 minutes. This slurry now contains 45 wt % solids, of which 40% being SAPO-34 sieve, 10.6% $ZrO_2$—$Al_2O_3$ (4.3% $ZrO_2$-6.3% $Al_2O_3$), and 49.4% clay. It was used for spray dry to produce spray dried catalysts.

Example 6.2

Spray drying the slurry of Example 6.1 was conducted using a Yamato DL-41 spray dryer (Yamato Scientific America, Orangeburg, N.Y.). An amount of 750 g of the slurry was spray dried. The spray dryer operated in a down spray mode using an atomization nozzle of 1 mm. The spray drying conditions are: feed rate: 40 g/min; inlet temperature: 350° C.; atomization pressure: 1 bar; carrier gas (nitrogen) flow at 60% of full setting. Spray dry products were collected in a cyclone. They were calcined in a muffle furnace at 650° C. in air for 2 hours. The calcined samples were used for attrition and particle size analysis. The spray dried product derived from Example 6.1 is labeled as SD-82. Attrition resistance of the spray dry product was determined using a jet-cup attrition unit. The hourly fines generation as a result of attrition thus obtained is defined as ARI (Attrition Resistance Index). See U.S. Pat. No. 6,872,680 for a complete description of the ARI method, which is incorporated herein by reference. A higher ARI means a higher attrition rate or a weaker product. SD-82 gave an ARI of 1.05%/hr.

Example 6.3

For comparison, spray dry of a slurry prepared using the same procedure except using an aluminum-only binder, Aluminum Chlorohydrate, USP, Chlorohydrol Micro-Dry (Reheis Inc., Berkeley Heights, N.J.) was carried. This spray dried product is labeled as SD-89. This product gave an ARI of 0.95%/hr.

Example 6.4

This example illustrates impact of aging. The slurry from Example 6.1 was aged at 40° C. under stirring at 250 rpm for 16 hours. Spray drying of the aged slurry is similar to that used in Example 6.2. An amount of 750 g of the aged slurry was spray dried. This spray dried product is labeled as SD-83. This sample gave an ARI of 0.43%/hr. Spray drying of the aged slurry produced a product having a substantially higher attrition resistance (ARI reduced from 1.05%/hr to 0.43%/hr).

Example 6.5

The slurry from Example 6.4 was further aged, but this time at room temperature for a total of 3 days. Conditions used for spray drying of this slurry is identical to that used in Example 6.2. An amount of 750 g of the aged slurry was spray dried. This spray dried product is labeled as SD-85. This product has an ARI of 0.20%/hr. This illustrates that flurther aging has also led to a substantial improvement in attrition resistance (ARI reduced from 0.43%/hr to 0.20%/hr).

Example 7

A catalyst of the type produced in Example 6.2, i.e., having a catalyst resistivity in a range of from $10^9$-$10^{11}$ ohm-cm, was used in a run according to the flow diagram as shown in FIG. 1, and using the calculating method of Example 1. The results are shown in Table 6.

TABLE 6

| | | Stream No. | | | | |
|---|---|---|---|---|---|---|
| | | 1 | 2 | 3 | 4 | 5 |
| Stream Description | | REGEN FLUE GAS | ESP INLET | COLLECTED FINES | STACK GAS | WASTE WATER STRIPPER BTMS |
| Stream Phase | | VAPOR | VAPOR | SOLID | VAPOR | LIQUID |
| Temperature | F. | 1200 | 582 | 530 | 500 | 302 |
| Pressure | PSIG | 18.0 | 1.0 | 0.4 | 0.0 | 54.6 |
| Total Flow Rates | LB/HR | | | | | |
| Vapor or Liquid | | 515209.8 | 515209.8 | 0.0 | 515209.8 | 1348736.0 |
| Coke | | 0.0 | 0.0 | 0.0 | 0.0 | 6.8 |
| Catalyst | | 8.6 | 8.6 | 8.1 | 0.5 | 164.2 |
| Total Mass Rate | LB/HR | 515218.5 | 515218.5 | 8.2 | 515210.4 | 1348907.0 |
| Vapor Rate | ACFH | 9686132.0 | 12663557.5 | — | 12460674.7 | — |
| | NM$^3$/hr | 180834.1 | 180834.1 | — | 180834.1 | — |
| Cat. Loading in Vapor | mg/NM$^3$ | 21.7 | 21.7 | — | 1.3 | — |
| Cat. Loading in Liquid | PPMW | — | — | — | — | 127 |
| Catalyst Particle Size Distribution Cumulative wt % less than | Microns | | | | | |
| 0.01 | | 0.09 | 0.09 | 0.07 | 0.10 | 0.03 |
| 0.1 | | 0.16 | 0.16 | 0.16 | 0.19 | 0.08 |
| 0.5 | | 0.25 | 0.25 | 0.29 | 0.29 | 0.16 |
| 1 | | 0.32 | 0.32 | 0.38 | 0.35 | 0.2 |
| 2 | | 0.41 | 0.41 | 0.50 | 0.41 | 0.4 |
| 3 | | 0.49 | 0.49 | 0.58 | 0.46 | 0.4 |
| 4 | | 0.55 | 0.55 | 0.65 | 0.50 | 0.5 |
| 5 | | 0.61 | 0.61 | 0.71 | 0.53 | 0.6 |
| 10 | | 0.85 | 0.85 | 0.92 | 0.64 | 1.1 |
| 20 | | 1.3 | 1.3 | 1.2 | 1.1 | 2.0 |
| 30 | | 1.7 | 1.7 | 1.4 | 1.4 | 4.0 |
| 40 | | 2.2 | 2.2 | 1.6 | 1.6 | 10.1 |
| 50 | | 2.8 | 2.8 | 2.5 | 1.9 | 16.0 |
| 60 | | 4.0 | 4.0 | 6.0 | 2.3 | 22.5 |
| 70 | | 9.0 | 9.0 | 12.7 | 2.7 | 30.1 |
| 80 | | 31.8 | 31.8 | 24.2 | 3.3 | 37.9 |
| 90 | | 48.7 | 48.7 | 42.8 | 3.9 | 46.8 |
| 95 | | 56.3 | 56.3 | 55.6 | 4.2 | 54.5 |
| 99 | | 67.8 | 67.8 | 67.9 | 4.6 | 71.1 |

Example 8

Figure 4:
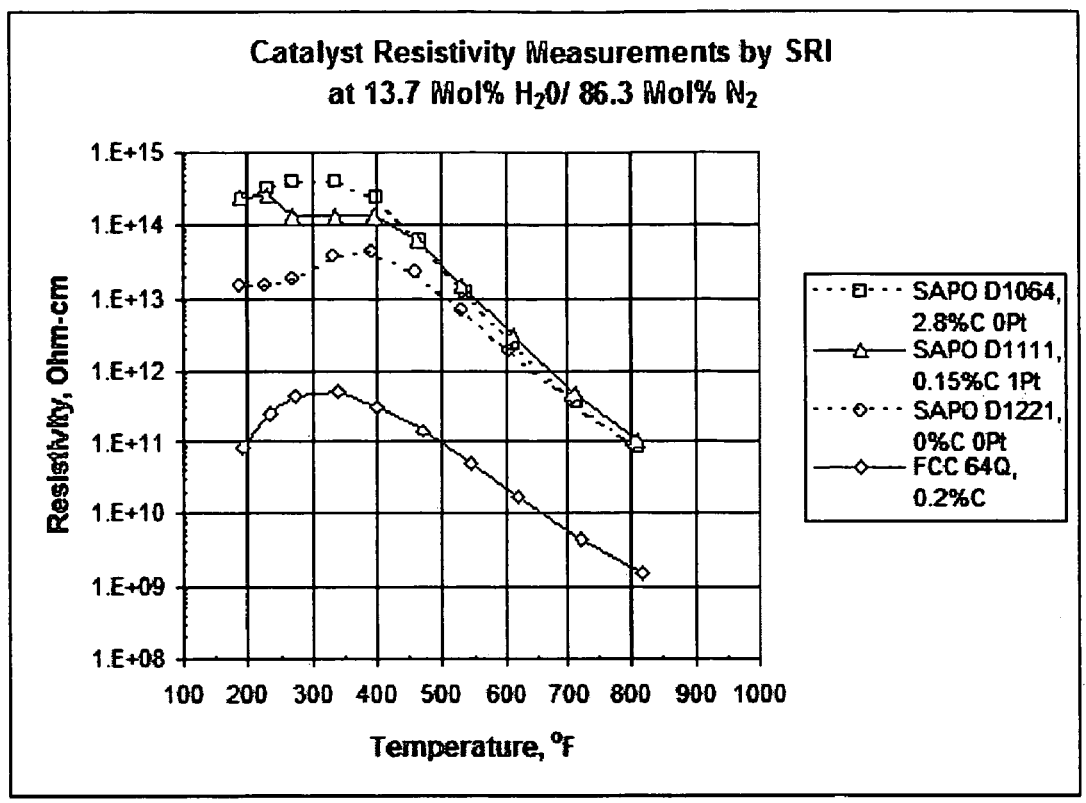
FIG. 4 is a graph comparing the resistivities of certain molecular sieve catalysts.

Three non-zeolitic, SAPO type catalysts and one zeolitic, FCC type catalyst were tested for resistivity. A comparison of the resistivities is shown in FIG. 4. It is found that the zeolitic, FCC type catalyst is more effectively separated from a gas stream in an ESP at lower temperatures relative to the non-zeolitic, SAPO catalyst.

The principles and modes of operation of this invention have been described above with reference to various exemplary and preferred embodiments. As understood by those of skill in the art, the overall invention, as defined by the claims, encompasses other preferred embodiments not specifically enumerated herein.

What is claimed is:

1. A process for removing silicoaluminophosphate molecular sieve catalyst particles containing [AlO$_4$] and [SiO$_4$] tetrahedral units from an oxygenate to olefin reaction system having a reactor and regenerator, comprising:
   a) exposing the molecular sieve catalyst particles to regeneration conditions to remove carbon;
   b) separating the molecular sieve catalyst particles from a flue gas stream in the regenerator so that the flue gas stream exits the regenerator at an average catalyst loading of greater than or equal to 10 mg/NM$^3$; and
   c) flowing the flue gas stream exiting the regenerator through a catalyst fine separation unit to form a final flue gas stream having an average catalyst loading of less than that of the stream exiting the regenerator;

wherein the catalyst fine separation unit is an electrostatic precipitator operated at a catalyst resistivity of not greater than $10^{12}$ ohm-cm and a temperature of at least 250° C.

2. The process of claim 1, wherein the catalyst is separated in the regenerator using a cyclone separation system.

3. The process of claim 1, wherein the molecular sieve catalyst comprises an electrostatic charging modifier that provides a catalyst resistivity of not greater than $10^{12}$ ohm-cm.

4. The process of claim 3, wherein the electrostatic charging modifier includes at least one metal oxide and the catalyst particles have a TOF$_{redox}$ of not greater than 1000 sec$^{-1}$, measured at 100° C.

5. The process of claim 3, wherein the electrostatic charging modifier is selected from the group consisting of $Cr_2O_3$, $V_2O_5$, $Fe_2O_3$, NiO, ZnO, $SnO_2$, $MoO_3$, $TeO_2$, $Sb_2O_3$, $ZrO_2$, and $CeO_2$.

6. The process of claim 1, wherein the molecular sieve catalyst comprises at least one metal oxide electrostatic charging modifier in an amount of at least 50 ppm, based on total weight of the catalyst.

7. The process of claim 1, wherein a gas stream is added to the electrostatic precipitator to provide a catalyst resistivity of not greater than $10^{12}$ ohm-cm.

8. The process of claim 1, wherein a water stream is added to the electrostatic precipitator and the electrostatic precipitator is operated at water dew point temperature.

9. The process of claim 1, wherein the catalyst fine separation unit is a filter unit and the filter unit is operated at an average temperature of from 100° C. to 450° C.

10. The process of claim 1, wherein the catalyst fine separation unit is a wet gas scrubber in which a water stream is injected into the scrubber to remove the catalyst particles and form the final flue gas stream.

11. The process of claim 10, wherein the water stream is taken from a bottoms stream of a methanol stripper.

12. The process of claim 1, wherein the process further comprises contacting the catalyst particles with an oxygenate stream in the reactor to form an olefin product, and contacting the olefin product with a water stream in a quench column to remove catalyst particles entrained in the olefin product.

13. The process of claim 12, wherein a water stream containing catalyst particles is removed from the quench column and sent to a methanol stripper.

14. The process of claim 13, wherein at least a portion of a bottoms water stream from the methanol stripper is sent to the fine separation unit.

15. A process for removing silicoaluminophosphate molecular sieve catalyst particles containing $[AlO_4]$ and $[SiO_4]$ tetrahedral units from an oxygenate to olefin reaction system having a reactor and regenerator, comprising:
  a) exposing the molecular sieve catalyst particles to regeneration conditions to remove carbon;
  b separating at least a portion of the catalyst particles from a flue gas stream in the regenerator so that the flue gas stream exits the regenerator at an average catalyst loading of from 10 mg/$NM^3$ to 200 mg/$NM^3$;
  c) flowing the flue gas stream exiting the regenerator through an electrostatic precipitator operated at a catalyst resistivity of not greater than $10^{12}$ ohm-cm; and
  d) recovering a final flue gas stream from the electrostatic precipitator having an average catalyst loading less than that of the flue gas stream from the regenerator;
wherein the molecular sieve catalyst comprises an electrostatic charging modifier that provides a catalyst resistivity of not greater than $10^{12}$ ohm-cm and a temperature of at least 250° C.

16. The process of claim 15, wherein the electrostatic precipitator is operated to produce a final flue gas having an average catalyst loading of less than 10 mg/$NM^3$.

17. The process of claim 15, wherein the catalyst is separated in the regenerator using a cyclone separation system.

18. The process of claim 15, wherein the electrostatic charging modifier is selected from the group consisting of $Cr_2O_3$, $V_2O_5$, $Fe_2O_3$, NiO, ZnO, $SnO_2$, $MoO_3$, $TeO_2$, $Sb_2O_3$, $ZrO_2$, and $CeO_2$.

19. The process of claim 15, wherein a gas stream is added to the electrostatic precipitator to provide a catalyst resistivity of not greater than $10^{12}$ ohm-cm.

20. The process of claim 15, wherein a water stream is added to the electrostatic precipitator and the electrostatic precipitator is operated at water dew point temperature.

21. The process of claim 15, wherein the process further comprises contacting the catalyst particles with an oxygenate stream in the reactor to form an olefin product, and contacting the olefin product with a water stream in a quench column to remove catalyst particles entrained in the olefin product.

22. The process of claim 21, wherein a water stream containing catalyst particles is removed from the quench column and sent to a methanol stripper.

23. The process of claim 21, wherein at least a portion of a bottoms water stream from the methanol stripper is sent to the fine separation unit.

24. A process for removing silicoaluminophosphate molecular sieve catalyst particles containing $[AlO_4]$ and $[SiO_4]$ tetrahedral units from an oxygenate to olefin reaction system having a reactor and regenerator, comprising:
  a) contacting the catalyst particles with an oxygenate stream in the reactor to form an olefin product;
  b) contacting the olefin product with a water stream in a quench column to remove catalyst particles entrained in the olefin product;
  c) exposing the molecular sieve catalyst particles to regeneration conditions to remove carbon;
  d) separating at least a portion of the catalyst particles from a flue gas stream in the regenerator so that the flue gas stream exits the regenerator at an average catalyst loading of from 10 mg/$NM^3$ to 200 mg/$NM^3$;
  e) flowing the flue gas stream exiting the regenerator through a catalyst fine separation unit; and
  f) recovering a final flue gas stream from the catalyst fine separation unit at an average catalyst loading less than that of the flue gas stream from the regenerator;
wherein electrostatic precipitator is operated at a catalyst resistivity of not greater than $10^{12}$ ohm-cm and a temperature of at least 250° C.

25. The process of claim 24, wherein the catalyst fine separation unit is operated to produce a final flue gas having an average catalyst loading of less than 10 mg/$NM^3$.

26. The process of claim 24, wherein the catalyst is separated in the regenerator using a cyclone separation system.

27. The process of claim 24, wherein the electrostatic precipitator is operated at a temperature of at least 700° C.

28. The process of claim 24, wherein the molecular sieve catalyst comprises an electrostatic charging modifier that provides a catalyst resistivity of not greater than $10^{12}$ ohm-cm.

29. The process of claim 28, wherein the electrostatic charging modifier is selected from the group consisting of $Cr_2O_3$, $V_2O_5$, $Fe_2O_3$, NiO, ZnO, $SnO_2$, $MoO_3$, $TeO_2$, $Sb_2O_3$, $ZrO_2$, and $CeO_2$.

30. The process of claim 24, wherein a gas stream is added to the electrostatic precipitator to provide a catalyst resistivity of not greater than $10^{12}$ ohm-cm.

31. The process of claim 24, wherein a water stream is added to the electrostatic precipitator and the electrostatic precipitator is operated at water dew point temperature.

32. The process of claim 24, wherein the catalyst fine separation unit is a filter unit and the filter unit is operated at an average temperature of from 100° C. to 450° C.

33. The process of claim 24, wherein the catalyst fine separation unit is a wet gas scrubber in which a water stream is injected into the scrubber to remove the catalyst particles and form the final flue gas stream.

34. The process of claim 33, wherein the water stream is taken from a bottoms stream of a methanol stripper.

* * * * *